(12) United States Patent
Beselt et al.

(10) Patent No.: US 8,742,385 B2
(45) Date of Patent: Jun. 3, 2014

(54) BEAM DISTORTION CONTROL SYSTEM USING FLUID CHANNELS

(75) Inventors: Ron Beselt, Burnaby (CA); Michael Wardas, North Vancouver (CA); Cris Andronic, Burnaby (CA)

(73) Assignee: Honeywell ASCa Inc., Mississauga (CA)

( * ) Notice: Subject to any disclaimer, the term of this patent is extended or adjusted under 35 U.S.C. 154(b) by 662 days.

(21) Appl. No.: 13/014,460

(22) Filed: Jan. 26, 2011

(65) Prior Publication Data

US 2012/0187317 A1 Jul. 26, 2012

(51) Int. Cl.
*G01N 21/89* (2006.01)
*G01N 21/86* (2006.01)

(52) U.S. Cl.
USPC .................. 250/559.45; 250/559.48

(58) Field of Classification Search
USPC .............. 250/559.4, 559.45, 559.48
See application file for complete search history.

(56) References Cited

U.S. PATENT DOCUMENTS

| | | | | |
|---|---|---|---|---|
| 3,348,046 | A | * | 10/1967 | Lloyd .................. 250/358.1 |
| 3,621,259 | A | * | 11/1971 | Boissevain ............. 250/360.1 |
| 3,754,146 | A | * | 8/1973 | Chow .................... 250/559.48 |
| 3,975,644 | A | * | 8/1976 | Scharf .................. 250/559.48 |
| 4,019,446 | A | * | 4/1977 | Abarotin et al. ........ 110/173 A |
| 4,276,480 | A | * | 6/1981 | Watson .................. 250/559.1 |
| 4,678,915 | A | * | 7/1987 | Dahlquist et al. ....... 250/358.1 |
| 4,823,590 | A | * | 4/1989 | Kniest et al. ............ 73/1.81 |
| 4,832,794 | A | | 5/1989 | Lyytinen |
| 4,879,471 | A | * | 11/1989 | Dahlquist .............. 250/359.1 |
| 4,914,309 | A | * | 4/1990 | Masaharu et al. ....... 250/559.48 |
| 4,947,684 | A | * | 8/1990 | Balakrishnan ............ 73/159 |
| 4,955,225 | A | * | 9/1990 | Kniest et al. ............ 73/597 |
| 4,955,433 | A | * | 9/1990 | Zaoralek ................ 165/89 |
| 5,040,773 | A | * | 8/1991 | Hackman ................ 266/87 |
| 5,117,093 | A | * | 5/1992 | Boissevain .............. 219/494 |
| 5,165,277 | A | * | 11/1992 | Bossen et al. ............ 73/159 |
| 5,166,748 | A | | 11/1992 | Dahlquist |
| 5,270,870 | A | | 12/1993 | O'Brien et al. |
| 5,579,836 | A | * | 12/1996 | Maruyama ............... 165/175 |
| 5,621,220 | A | * | 4/1997 | Muehlenbein et al. .. 250/559.48 |
| 5,654,799 | A | | 8/1997 | Chase et al. |
| 5,773,714 | A | | 6/1998 | Shead |
| 5,793,486 | A | | 8/1998 | Gordon et al. |
| 6,433,310 | B1 | * | 8/2002 | Wickramasinghe et al. . 219/216 |
| 6,466,409 | B1 | | 10/2002 | Baba et al. |
| 7,494,567 | B2 | | 2/2009 | Haran |
| 7,751,918 | B2 | | 7/2010 | Campbell et al. |
| 2002/0101812 | A1 | * | 8/2002 | Wickramasinghe et al. ... 369/99 |
| 2002/0134542 | A1 | * | 9/2002 | Unsworth ............... 165/277 |
| 2004/0262549 | A1 | * | 12/2004 | Chaudhary et al. ....... 250/559.45 |
| 2007/0029642 | A1 | | 2/2007 | Inagawa et al. |
| 2007/0034360 | A1 | * | 2/2007 | Hall ................... 165/104.33 |
| 2012/0187317 | A1 | * | 7/2012 | Beselt et al. ............. 250/559.01 |

* cited by examiner

*Primary Examiner* — John Lee
(74) *Attorney, Agent, or Firm* — Cascio Schmoyer & Zervas

(57) ABSTRACT

Paper and continuous web scanners operate at varying and high temperature conditions that cause distortion of the support beams and ultimately misalignment of the scanner heads. Circulating a heat transfer fluid between the support beams and through segmented fluid channels within the beam allows tuning of the beam's deflection when operating in an uneven thermal environment. The heat transfer rate can be modulated through various techniques, including: (1) varying the flow rate through each channel under manual or automatic control, (2) controlling the inlet fluid temperature of each channel with fluid immersion heaters or coolers, and (3) setting up the flow sequence via distribution channels that are, for example, in parallel, serial, or mixed.

17 Claims, 4 Drawing Sheets

BEAM DISTORTION CONTROL SYSTEM USING FLUID CHANNELS

FIELD OF THE INVENTION

The present invention generally relates to scanner measurement systems for determining parameters of continuous sheet materials during production and, more particularly, to techniques for maintaining the alignment of dual scanner heads by controlling the temperature profiles of their support beams through selective distribution of a heat transfer medium through segmented fluid channels within the beams.

BACKGROUND OF THE INVENTION

Various sensor systems have been developed for detecting sheet properties "on-line," i.e., on a sheet-making machine while it is operating. Sensors for continuous flat sheet production processes typically employ single or dual-sided packages with on-line sensors that traverse or scan traveling webs of sheet material during manufacture. With dual scanners, the heads or assemblies are fixed to beams that span both sides of the sheet with linear guidance tracks to allow the sensors to move in unison in the cross direction, i.e., in the direction perpendicular to the direction of sheet travel. Depending upon the sheet-making operation, cross-directional distances can range up to about twelve meters or more. In the paper making art, for instance, the on-line sensors detect variables such as basis weight, moisture content, and caliper of sheets during manufacture.

On-line measurements are difficult to make accurately. In the case where the sensor comprises dual scanner heads, under normal operating conditions the alignment of the upper and lower track systems are similar to factory alignment. However, if the mill-operating environment exposes the beams to uneven thermal loading, the upper and lower sensor paths will deviate from factory specifications. This will cause variations in sensor readings across the width of the sheet.

SUMMARY OF THE INVENTION

The present invention is directed to techniques for controlling the temperature profiles of the support beams in dual scanner systems in order to minimize beam distortion. Paper and continuous web scanners are often operated at varying and high temperature conditions. Thermal loading originate from a myriad of sources in the proximity of the scanner that cause ambient air temperature gradients between the beams that are positioned above and below the sheet of paper. Major contributors include hot or cold air sources, such as exterior doors, openings to cold basements, and hot drier exits, and directional heating from infrared radiation sources typically used to dry coatings on sheets. The temperature fluctuations cause beam distortion that adversely affect the sensors that measure, for example, the basis weight, thickness, and composition of the moving sheet.

To address this problem, with the present invention, segmented fluid channels are incorporated into the support beam, and by selectively distributing a heat transfer medium through the channels, beam distortion can be significantly reduced or eliminated. The invention is based in part on the recognition that in order to minimize temperature-induced distortions in large-scale industrial dual sensor systems where the support beams have large cavities, it is necessary to employ a segmented fluid design where individual channels are strategically integrated into different regions of the beam such as, for instance, the side, top and bottom interior surfaces of the beam cavity. By controlling the heat transfer rate in the channels, the beam's deflection can be tuned when operating in an uneven thermal environment. The heat transfer fluid is not simply circulated in a closed loop between the cavities of the upper and lower beam structures in hope of equalizing the temperature of the metal beams. Rather, with the present invention, the heat transfer rate can be modulated through various techniques, including, for instance: (1) varying the flow rate through each channel under manual or automatic control, (2) controlling the inlet fluid temperature of each channel with fluid immersion heaters or coolers, and (3) setting up the flow sequence via distribution channels that are, for example, in parallel, in series, or combinations.

In one aspect, the invention is directed to beam system for supporting one or more mounted carriages that moves along defined paths, which includes:

a first elongated member that extends along a first direction wherein the first elongated member includes a plurality of first fluid channels therein and the first elongated member supports a first carriage that is mounted thereon;

a second elongated member that extends along a second direction that is parallel to the first direction wherein the second elongated member includes a plurality of second fluid channels therein and the second elongated member supports a second carriage that is mounted thereon; and means for delivering a fluid through the first and second fluid channels to control the temperatures of the first and second elongated members.

In another aspect, the invention is directed to a system for measuring properties of the composition of traveling webs of sheet material during manufacture, which includes:

a first track means mounted to extend generally parallel to one face of a traveling web in the cross direction wherein the first track means includes a plurality of first fluid channels therein;

a first sensor device that is mounted on the first track means and that moves along the cross direction;

a second track means mounted to extend generally parallel to the first track means adjacent the opposite face of the web wherein the second track means includes a plurality of second fluid channels therein;

second sensor device that is mounted on the second track means and that moves along the cross direction, wherein the first and second sensor devices are aligned as they move back and forth along the cross direction; and means for delivering a modulated fluid heat transfer medium through the first and second fluid channels in response to environmental temperature gradients to which the first and second track means are exposed.

In yet another aspect, the invention is directed to a method of compensating for structural distortions in a scanning system that are caused by uneven thermal environment of the scanning system that measures properties of traveling webs of sheet material during manufacture, wherein the scanning system includes:

a first track means mounted to extend generally parallel to a face of a traveling web in the cross direction a radiation source that is mounted on the first track means and moves along the cross direction and that directs radiation onto the face of the traveling web;

a second track means mounted to extend generally parallel to the first track means adjacent an opposite face of the web; and a radiation detector that is mounted on the second track means and moves along the cross direction and that detects radiation transmitted through the web, wherein the method includes the steps of:
(a) forming a plurality of first fluid channels in the first track means;
(b) forming a plurality of second fluid channels in the second track means; and
(c) distributing a fluid heat transfer medium through the plurality of first and second fluid channels in order to reduce temperature differential between the first track means and the second track means in order to maintain alignment of the radiation source and the radiation detector as the radiation source and radiation detector move along the cross direction.

DESCRIPTION PREFERRED EMBODIMENTS

Figure 1:
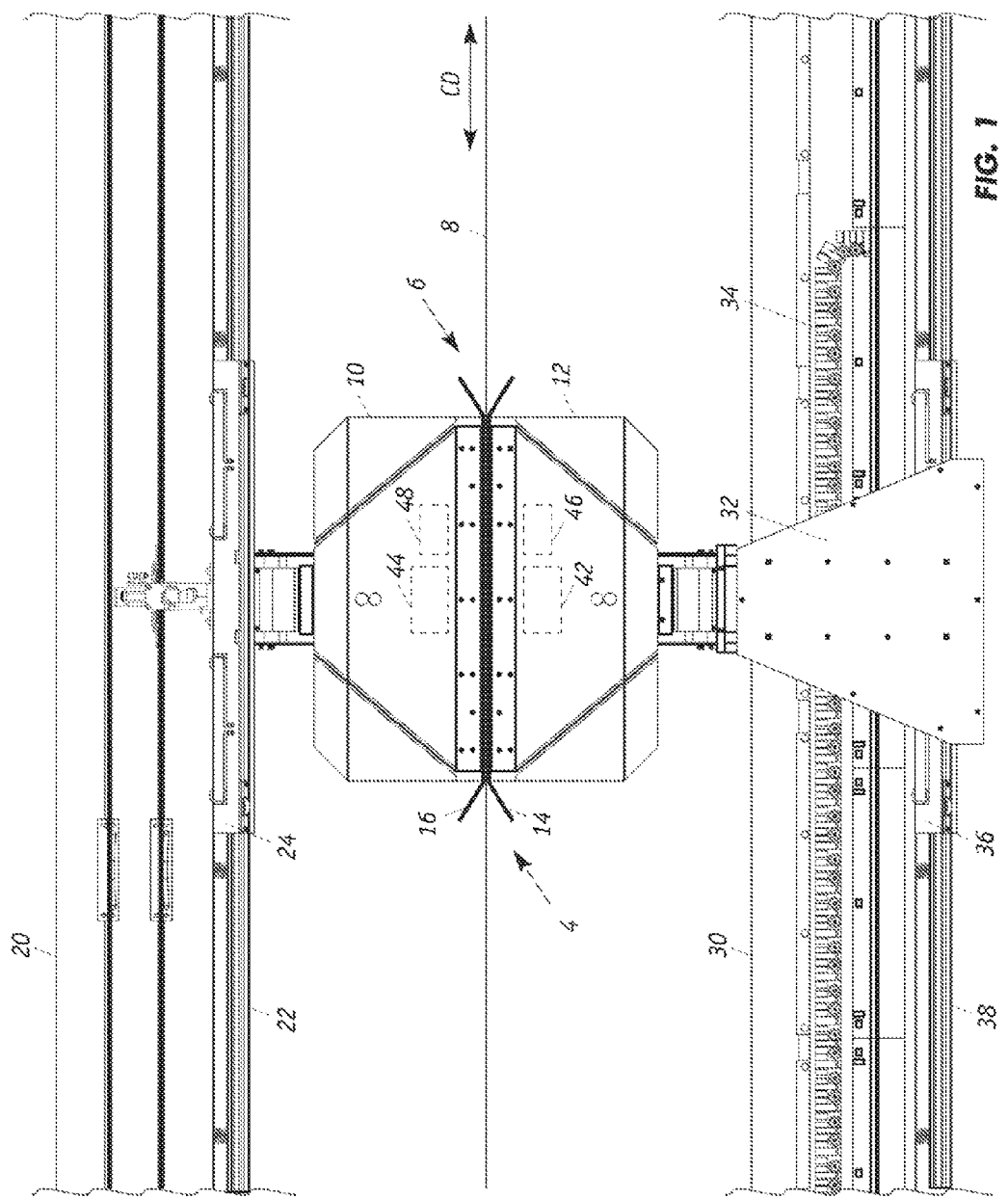
FIG. 1 illustrates a scanner system employing dual sensor heads.

FIG. 1 shows a scanning system with scanner sensor heads 10 and 12. This dual scanner head configuration is typically employed when the sensor is operating in the transmission mode. For example, upper sensor head 10 may house a source of infrared radiation 44 while the lower sensor head 12 houses an infrared detector 42 that measures the radiation that is transmitted through the material being monitored. Alignment sensors 46, 48 which are described, for example, in U.S. Pat. No. 5,714,763 to Chase et al., generate misalignment measurements of the scanner heads.

Upper scanner head 10 is supported by an upper support beam 20 that has a lower surface to which a series of laterally spaced apart rigid support structures is mounted. These vertical structures support track 22. A roller carriage 24 engages track 22 as the carriage advances along the cross direction to a moving sheet 8. The lower scanner head 12 is supported by a lower support beam 30 that has a lower surface on which a plurality of laterally spaced apart rigid support structures is mounted. Upper and lower support beams 20, 30 are mounted onto a pair of upright end members (not shown).

Movement of the roller carriage is facilitated by a drive mechanism similar to that of the upper scanner head. Vertical structures also support track 38 onto which carriage 36 is engaged. A power chain 34 supplies electricity and electrical signal to lower scanner head 12. Lower sensor head 12 is mounted on a member 32 that extends from roller carriage 36 so as to position lower sensor head 12 adjacent to upper scanner head 10. The operative faces or plates 14, 16 of the lower and upper scanner heads 12, 10 define a measurement gap through which a web of material 8, such as paper, moves. Lateral openings 4 and 6 of the measurement gap allow the scanner to move in the cross direction (CD) as the paper travels in the machine direction. The movement of the dual scanner heads 10, 12, is synchronized with respect to speed and direction so that they are aligned with each other. Scanning systems having sensor components on opposite sides of the sheet being analyzed are described, for example, in U.S. Pat. No. 5,773,714 to Shead and U.S. Pat. No. 5,166,748 to Dahlquist, which are incorporated herein by reference.

Scanner heads 10, 12 serve as platforms for carrying sensors to detect sheet properties, such as basis weight, in the case of paper. For example, lower scanner head 12 may carry a radiation source, such as a nuclear beta radian source, and upper scanner head 10 may carry a detector. In this case, the sensors can be employed to make basis weight measurements by measuring the radiation intensity incident on the detector when a sheet is present as compared to the beta radiation that is incident upon the detector, when no sheet is present; that is, the basis weight is measured by the beta radiation attenuated by the sheet material.

Alternatively, to measure the moisture content of paper, an infrared radiation source can be positioned in the lower scanner head 12 and the radiation that is transmitted through the paper is captured by a detector that is located in the upper scanner head 10. Analysis of the transmitted radiation yields the moisture content. Exemplary scanning dual head sensors employing radiation source and detectors are described, for example, in U.S. Pat. No. 5,654,799 to Chase et al., U.S. Pat. No. 5,793,486 to Gordon et al., and U.S. Pat. No. 7,494,567 to Haran, which are incorporated herein by reference.

Figure 2:
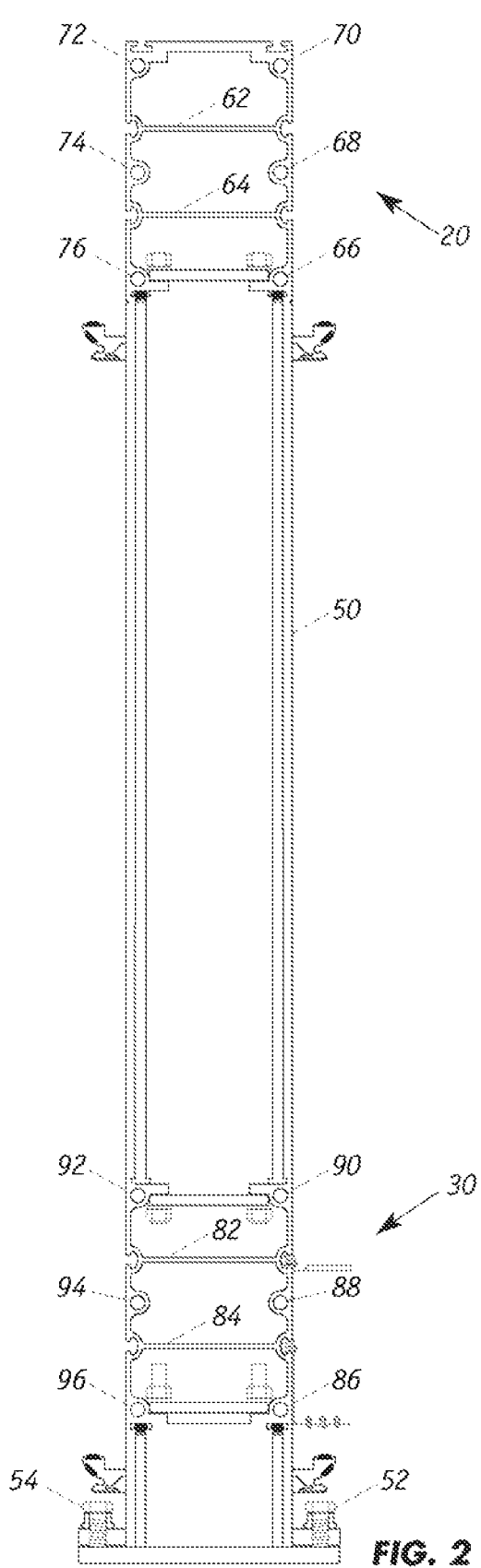
FIG. 2 is a cross sectional end view of the support beams of the dual scanning sensor illustrating the segmented fluid channels.

As shown in FIG. 2, upper and lower structural support beams 20, 30 are mounted to a vertical end member 50 that is secured with bolts 52, 54 to a factory floor. Each single monolithic beam, with its hollow cross section, is preferably manufactured from extruded aluminum. In upper support beam 20, web members 62, 64 add structural integrity and provide lateral support during the extrusion manufacturing process by keeping the sides of the beam from deforming. In this embodiment, upper beam structure 20 has six segmented fluid channels 66, 68, 70, 72, 74 and 76 distributed in the interior surface of the hollow cavity. Similarly, lower beam structure 30 includes interior web member 82, 84 and has six segmented fluid channels 86, 88, 90, 92, 94 and 96. Typically, each support beam has 2 to 8 or more segmented fluid channels. The number of channels will depend on the size and length of the beams with more channels being employed to provide sufficient fluid coverage if the beams are larger and/or longer. The lengths of support beams 20, 30 typically range from 6 to 14 meters and more. Typically, the channels are dimensioned so that they collectively accommodate closed-loop fluid flow rates of 20 to 200 liters per minute of a non-corrosive, liquid heat transfer medium such as a mixture of glycol and water.

FIGS. 3A, 3B, 3C and 3D depict alternative channel layouts within upper and lower structural support beams that are mounted to a vertical end member (not shown). The configurations of the segmented fluid channels are designed to allow tuning of the beam's deflection. In particular, different directional influences can be achieved by selecting the appropriate fluid channel placement.

Figure 3A:
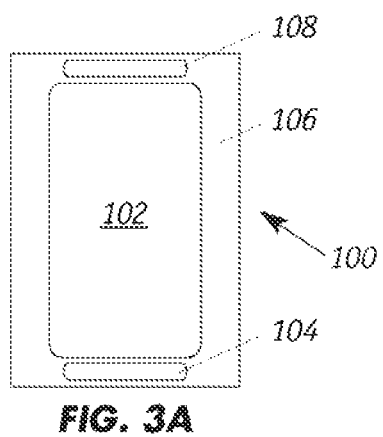
FIGS. 3A, 3B, 3C and 3D illustrate the cross sections of different segment arrangements in support beams.

FIG. 3A shows the cross section of beam arrangement 100 which includes beam structure 106 having lower and upper fluid channels 104, 108 and cavity 102. Each fluid channel preferably defines an elongated aperture that is formed along the lower or upper side of the beam structure. This arrangement is particularly suited to offset or prevent beam deflection along the vertical direction, in other words, this arrangement allows an operator to affect the lower and upper beam surfaces. In particular, as a modulated fluid heat transfer medium passes through the lower and upper channels 104, 108, the temperature along the lower and upper sides of the beam is maintained at a desired range thereby affording camber control along the width of beam structure 106.

Figure 3B:
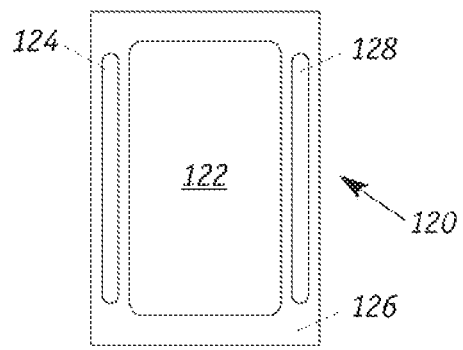

Similarly, FIG. 3B shows the cross section of beam arrangement 120 which includes beam structure 126 having first and second lateral fluid channels 124, 128 and cavity 122.

Each fluid channel defines an elongated aperture that is formed along a lateral side of the beam structure. This arrangement is particularly suited to correct side-to-side bow. As modulated fluid heat transfer medium passes through the lateral channels 124, 128, the temperature along the lateral sides of the beam is maintained at a desired range thereby affording bow control along the length of beam structure 126.

Figure 3C:
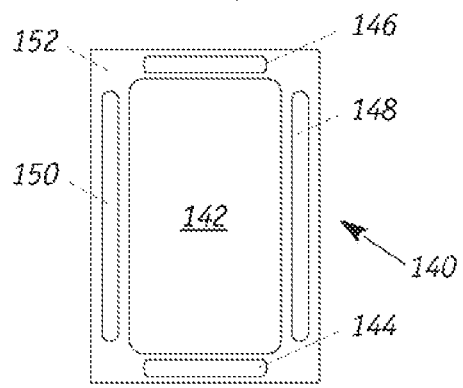
Figure 3D:
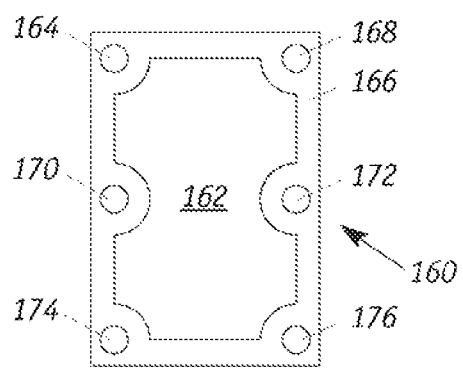

FIG. 3C shows the cross section of beam arrangement 140 which includes beam structure 152 having both lower and upper fluid channels 144, 146 and lateral fluid channels 148, 150 and cavity 142. This configuration permits simultaneous bow and camber control. Finally, FIG. 3D is an alternative configuration for combined bow and camber control in which beam arrangement 160 includes beam structure 166 and fluid channels 164, 168, 170, 172, 174 and 176 and cavity 162. Each channel preferably has a circular cross section which is easier to connect with a fitting than channels that are long and wide. In operation, the pair of upper fluid channels 164, 168 and the pair of lower fluid channels 174. 176 are used for camber control of the upper and lower sides, respectively. Likewise, fluid channels 164, 170 and 174 are used for bow control of the first lateral side whereas fluid channels 168, 172, and 176 are used for bow control of the second lateral side. The combined control affects all four surfaces of beam structure 160.

Figure 4:
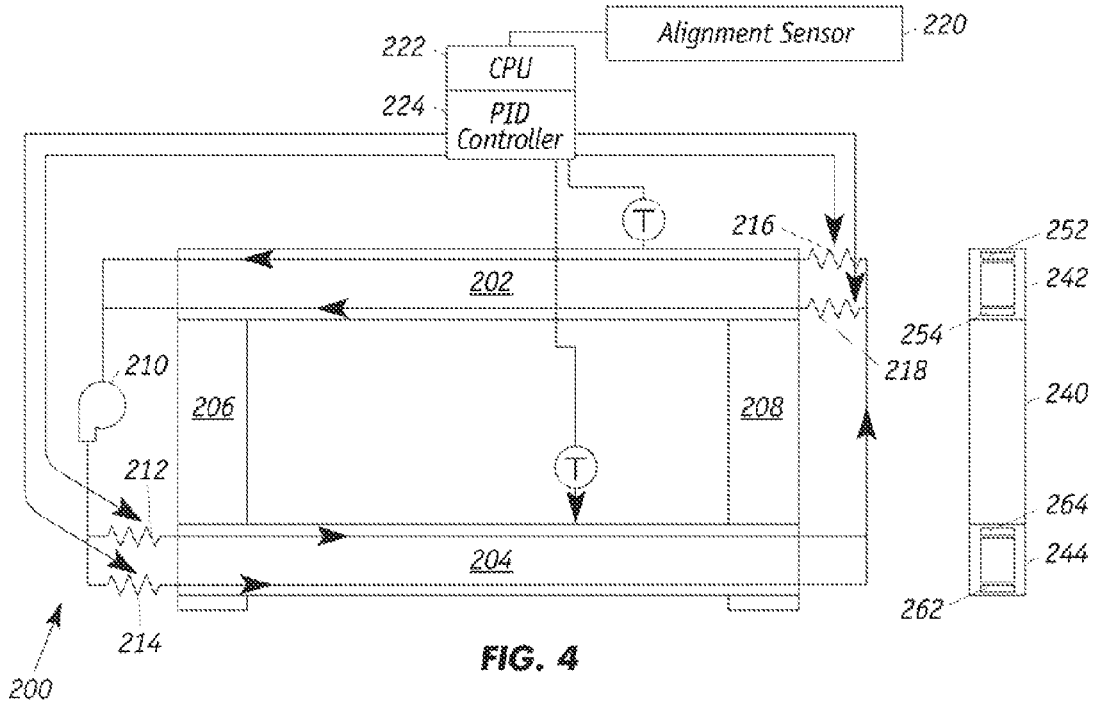
FIGS. 4-7 are schematics of beam distortion control systems.

Modulation of heat transfer within the fluid channels can be achieved by a number of techniques, including for example, regulating the temperature and/or flow rate of the fluid heat transfer medium and appropriate channel coupling of the upper to lower (or lower to upper) sets of fluid channels. FIG. 4 depicts a control system 200 for controlling beam distortion in a scanner system that includes an upper support beam 202 and a lower support beam 204 that are held by vertical end members 206, 208. Carriages (not shown) are mounted to the support beams. As shown in cross section, the upper beam structure 242 includes upper and lower fluid channels 252, 254 whereas the lower beam structure 244 includes upper and lower fluid channels 264, 262. The upper and lower beam structures are separated by vertical member 240. With its two upper and lower fluid channels in each of the beam structures, this configuration, like the channel layout shown in FIG. 3A, is particularly suited for camber control. By using different channel layouts, this control system can be readily modified to achieve bow control or expanded to achieve combined camber and bow control.

As further illustrated in FIG. 4, only two channels are employed for illustrative purposes, and in this arrangement, fluids in the channels of the upper support beam 202 are mixed and then delivered by pump 210 into the channels in the lower support beam 204. On the return route, fluids in the channels of lower support beam 204 are mixed and then diverted to the channels in upper support beam 202. Fluid is heated or cooled by conduction as needed in heat exchangers 212, 214 just before entering the fluid channels in lower support beam 204 and in heat exchangers 216 and 218 as needed just before entering the fluid channels in upper support beam 202.

Control system 200 further includes alignment sensors 220 that are positioned on scanner heads 10, 12 (FIG. 1) and microprocessor (CPU) 222 where set points such that the measurement gap height(s) between scanner heads 10, 12 are stored. In operation, feedback signals from alignment sensors 220 are compared to set points and proportional-integral-derivative (PID) controller 224 adjust actuators in heat exchanger elements 212, 214, 216, and 218. Control system 200 minimizes the temperature disparity between beams 202 and 204 and thereby maintains sensor misalignment within acceptable levels. While PID controllers are illustrated, it is understood that other controllers such as multivariable controllers may be required especially if the control is expanded to include additional channels, to implement side-to-side bow control, or to implement a combination bow and camber control.

Instead of responding to changes in the alignment in scanner heads 10, 12, the control system 200 can maintain the temperature of upper and lower support beams 202, 204 within predetermined temperature ranges. In this configuration, the adjustments in heat exchanges are made in response to temperature measurements of the beams.

Figure 5:
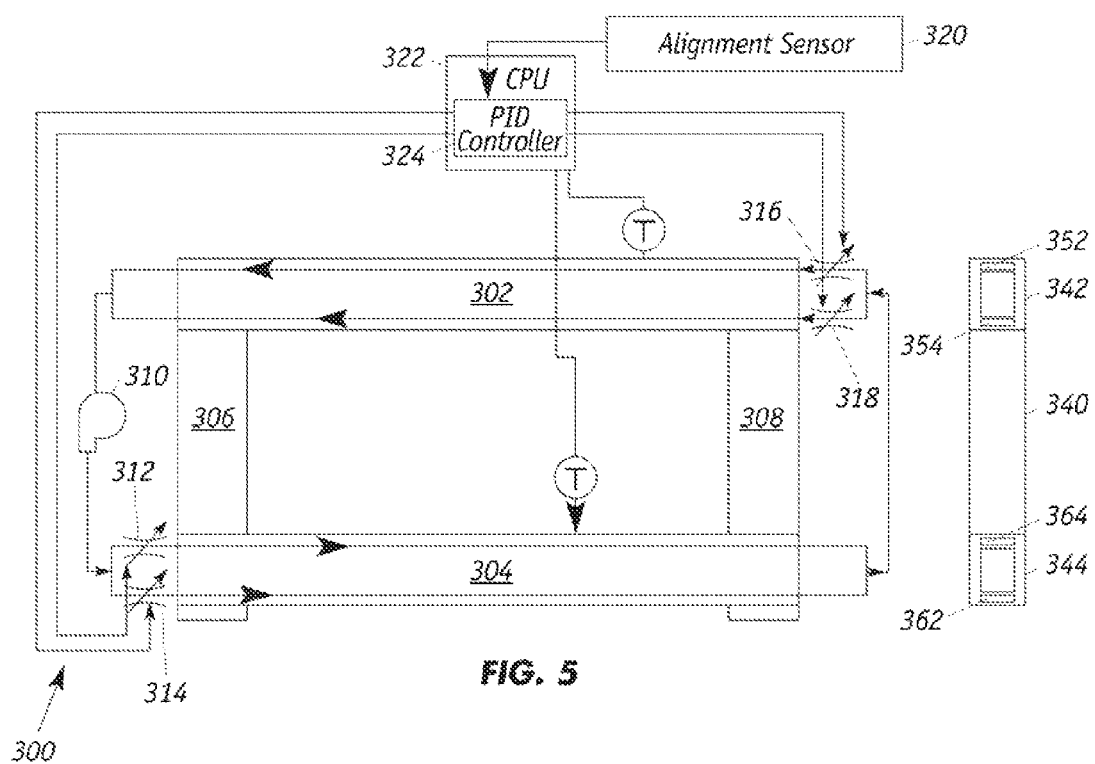

FIG. 5 depicts a control system 300 for controlling beam distortion by modulating the flow rate of the heat transfer medium in the channels in a scanner system that includes an upper support beam 302 and a lower support beam 304 that are held by vertical end members 306, 308. As shown in cross section, the upper beam structure 342 includes upper and lower fluid channels 352, 354 whereas the lower beam structure 344 includes upper and lower fluid channels 364, 362. The upper and lower beam structures are separated by vertical member 340. In this arrangement, fluids in the channels of the upper support beam 302 are mixed and then delivered by pump 310 into the channels of lower support beam 304. Manual or activated flow control valves 312 and 314 regulate the flow of the heat transfer medium into the upper and lower fluid channels, respectively, in the lower support beam 304. On the return route, fluids in the channels of lower support beam 304 are mixed and then diverted to the channels in upper support beam 302. Manual or activated flow control valves 316, 318 regulate the flow of the heat transfer medium into the upper and lower fluid channels, respectively, of upper support beam 302.

Control system 300 further includes alignment sensors 320 that are positioned on scanner heads 10, 12 (FIG. 1) and microprocessor (CPU) 322 where set points such that the measurement gap height(s) between scanner heads 10, 12 are stored. In operation, feedback signals from alignment sensors 320 are compared to set points and proportional-integral-derivative (PID) controller 324 adjust actuators in flow control devices 312, 314, 316, and 318. Instead of responding to changes in the alignment in scanner heads 10, 12, the control system 200 can maintain the temperature of upper and lower support beams 302, 404 within predetermined temperature ranges. In this configuration, the adjustments in flow regulators are made in response to temperature measurements of the beams.

If a large scanner system is housed in a mill where the temperature gradient from the cold factory floor to the top of the upper beam is significant, it may be more energy efficient to selectively couple segmented fluid channels in the top beam to those in the lower beam. For example, referring to FIG. 2, segmented fluid channels 70 and 72 from top beam 20 can be connected to segmented fluid channels 86 and 96, respectively. In this fashion, fluid flows from the hottest region of upper beam 20 to the coolest region of lower beam 30. To complete the flow design, channels 68 and 74 from upper beam 20 would be coupled to channels 88 and 94, respectively, in lower beam 30; and channels 66 and 76 from upper beam 20 would be coupled to channels 90 and 92, respectively, in lower beam 30. In this configuration, there would be 6 closed-loop channels with associated pumps. However, by combining each pair of channels in a single line while in-between beams as shown in FIG. 2, only 3 channels and pumps are required.

As is apparent, with the present invention, by intelligently modulating the heat transfer rate in the segmented channels within the support beam structures via control of flow rate, inlet fluid temperature and/or tube connection configurations between beams, it is expected that environmental heat loading can be compensated for whether the environmental heat loading is very localized or extreme. By selectively heating or cooling beam surfaces with the segmented channels it is possible that the beam curvature can be altered in a controlled fashion.

Figure 6:
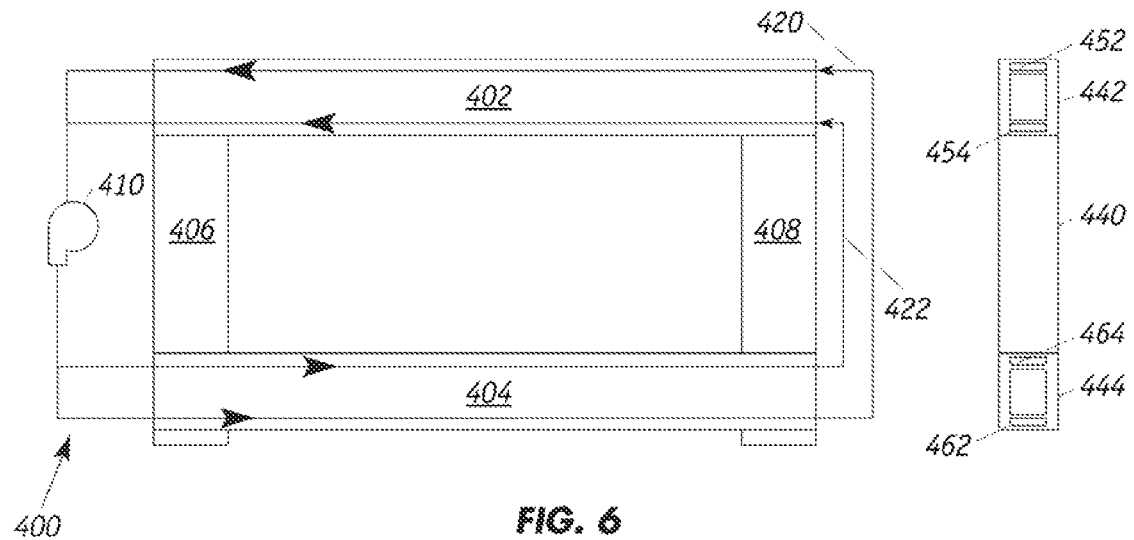

Beam distortion control can also be achieved in some instances by simply circulating fluid between the upper and lower support beams in a passive manner without any external heating or cooling. FIG. 6 shows a scanner system that includes upper and lower support beams 402, 404 that are held by vertical end members 406, 408. As shown in cross section, the upper beam structure 442 includes upper and lower fluid channels 452, 454 whereas the lower beam structure 444 includes upper and lower fluid channels 464, 462. The upper and lower beam structures are separated by vertical member 440. In this arrangement, fluids exiting the channels of upper support beam 402 are mixed and then delivered by pump 410 into the channels of lower support beam 404. The mixing action causes the fluid to be at the same temperature as it enters channels 462, 464. Fluid from upper fluid channel 464 of lower support beam 404 is transferred via line 422 to lower fluid channel 454 of upper support beam 402 whereas fluid from lower fluid channel 462 of lower support beam 404 is transferred via line 420 to upper fluid channel 452 of upper support beam 402. This layout of the channels is particularly suited for instance where the floor (adjacent channel 462) is very cold as compared to the ceiling (above channel 452). In this fashion, the colder fluid from channel 462 of the lower support beam is introduced into the warmer channel 452 of the upper support beam.

Figure 7:
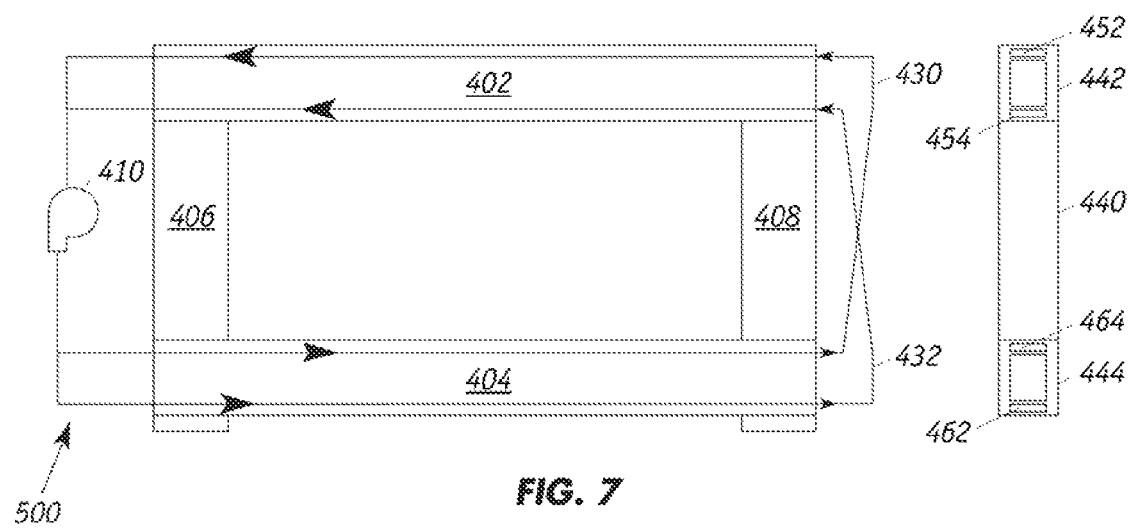

FIG. 7 shows the same beam structure configuration as that in FIG. 6 except in this arrangement fluids fluid from upper fluid channel 464 of lower support beam 404 is transferred via line 430 to upper fluid channel 452 of upper support beam 402 whereas fluid from lower fluid channel 462 of lower support beam 404 is transferred via line 432 to lower fluid channel 455 of upper support beam 402. This layout of the channels is particularly suited for instance where the floor (adjacent channel 462) is cold and where the lower surface of upper support beam 402 is colder than the upper surface of support beam 402.

As is apparent, the systems of FIGS. 6 and 7 are effective even when it is operated in a passive manner without any external heating or cooling by heat exchangers. For instance, if upper support beam 402 is exposed to elevated temperatures whereas lower support beam 404 is exposed to lower temperatures, then the continuous circulation of the heat transfer fluid through the system may be sufficient to control beam distortion. In this fashion, when the fluid is not temperature controlled, the fluid and beam structures are simply allowed to come to an equilibrium state. Any environmental thermal loading on the top beam, for instance, will be transferred by the fluid to bottom beam. If the heat transfer coefficients of aluminum and that of the circulating fluid are much higher than the uneven heat transfer rate from the environment, then a significant temperature gradient in the structure cannot be maintained since the energy is being transferred around between beam structures by the circulating fluid so quickly.

As an example, if the upper beam is in an ambient environment of 60° C., due to its location above a hot sheet, and the lower beam is in an ambient environment of 30° C., due to its proximity to cool floor concrete, then the action of the circulating fluid will attempt to transfer heat from the upper beam to the lower beam. Heated fluid from the top beam is circulated then through the lower beam to heat the lower beam higher than ambient. Eventually an equilibrium between all the heat transfer rates is achieved with the entire system operating at near the average of the two operating temperatures (60+30)/2=45° C. If the volume and/or circulation rate of the fluid are fast enough, the fluid will be able to move enough energy from the upper beam without changing fluid temperature significantly, for instance, less than 0.5° C., thereby affording both beams to be stabilized at nearly the same temperature.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A system for measuring properties of the composition of traveling webs of sheet material that are moving in a machine direction during manufacture, which comprises:
   a first track mounted to extend in a cross direction, which is perpendicular to the machine direction, and adjacent to a face of a traveling web wherein the first track comprises a first elongated monolithic member with a first upper wall, a first lower wall and first and second side walls and a plurality of first segmented fluid channels that are integrated into two or more walls of the first monolithic member which has a rectangular cross section and hollow cavity;
   a first sensor device that is mounted on the first track and that moves along the cross direction;
   a second track mounted to extend generally parallel to the first track and adjacent a second face of the traveling web that is opposite the first face of the traveling web wherein the second track comprises a second elongated monolithic member with a second upper wall, a second lower wall and third and fourth side walls and a plurality of second segmented fluid channels that are integrated into two or more walls of the second monolithic member which has a rectangular cross section and hollow cavity;
   a second sensor device that is mounted on the second track and that moves along the cross direction, wherein the first and second sensor devices are aligned as they move back and forth along the cross direction; and
   means for delivering a modulated fluid heat transfer medium through the plurality of first and second segmented fluid channels in response to environmental temperature gradients to which the first and second track are exposed such that the fluid heat transfer medium is in direct thermal communication with the first and second monolithic members.

2. The system of claim 1 comprising means for measuring the alignment of the first and second sensor devices as the move back and forth along the cross direction.

3. The system of claim 1 wherein the means for delivering the modulated fluid heat transfer medium selectively heats or cools heat transfer medium as it enters or exits one or more of the plurality of first and second segmented fluid channels.

4. The system of claim 1 wherein the plurality of first segmented fluid channels comprise from 2 to 8 first individual fluid channels and the plurality of second segmented fluid channels comprise from 2 to 8 second individual fluid channels.

5. The system of claim 1 wherein the flow rate of fluid heat transfer medium through the plurality of first and second segmented fluid channels ranges from 20 to 200 liters per minute.

6. The system of claim 1 wherein the first sensor device includes a radiation source that directs radiation onto the first face of the traveling web and wherein the second sensor device includes radiation detector that detects radiation transmitted through the traveling web and the radiation source moves back and forth along the cross direction in registration with the radiation detector.

7. A method of compensating for structural distortions in a scanning system that are caused by uneven thermal environment of the scanning system that measures properties of traveling webs of sheet material that are moving in a machine direction during manufacture, wherein the scanning system includes:
 a first track mounted to extend in a cross direction, which is perpendicular to the machine direction, and adjacent to a first face of a traveling web wherein the first track comprises a first elongated monolithic member with a first upper wall, a first lower wall and first and second side walls and which has a rectangular cross section and hollow cavity;
 a radiation source that is mounted on the first track and moves along the cross direction and that directs radiation onto the first face of the traveling web;
 a second track mounted to extend generally parallel to the first track and adjacent a second face of the traveling web that is opposite the first face of the traveling web wherein the second track comprises a second elongated monolithic member with a second upper wall, a second lower wall and third and fourth side walls and which has a rectangular cross section and hollow cavity; and
 a radiation detector that is mounted on the second track and moves along the cross direction and that detects radiation transmitted through the traveling web, wherein the method comprises the steps of:
 (a) forming a plurality of first segmented individual fluid channels that are integrated into two or more walls of the first elongated monolithic member;
 (b) forming a plurality of second segmented individual fluid channels that are integrated into two or more walls of the second elongated monolithic member; and
 (c) distributing a fluid heat transfer medium through the plurality of first and second segmented individual, fluid channels in order to reduce temperature differential between the first track and the second track and to maintain alignment of the radiation source and the radiation detector as the radiation source and radiation detector move along the cross direction.

8. The method of claim 7 wherein the first track is subject to first fluctuating environmental conditions with attendant temperature changes and the second track is subject to second fluctuating environmental conditions with attendant temperature changes.

9. The method of claim 8 wherein step (c) comprises (i) selectively heating or cooling the plurality of first segmented individual fluid channels with the fluid heat transfer medium and (ii) selectively heating, or cooling the plurality of second segmented individual fluid channels with the fluid heat transfer medium as necessary to maintain alignment of the radiation source and radiation detector at a predetermined range of alignment.

10. The method of claim 8 wherein step (c) comprises (i) heating or cooling the first track and (ii) selectively heating or cooling the second track as necessary to tune deflection of the first track and/or the second track in response to first and second fluctuating environmental conditions.

11. The method of claim 8 wherein step (c) comprises regulating the flow rates of the fluid heat transfer medium through the plurality of first and second segmented individual fluid channels.

12. The system of claim 1 wherein the first and second side walls of the first elongated monolithic member define exterior portions that are exposed to the environmental temperature gradients and the plurality of first segmented fluid channels are integrated into the first and second side walls and wherein the second and third side walls of the second elongated monolithic member define exterior portions that are exposed the environmental temperature gradients and the plurality of second segmented fluid channels are integrated into the third and fourth side walls.

13. The system of claim 1 wherein the first and second side walls of the first elongated monolithic member define exterior portions that are exposed the environmental temperature gradients and the plurality of first segmented fluid channels are integrated into each of the walls of the first elongated monolithic member and wherein the second and third side walls of the second elongated monolithic member define exterior portions that are exposed the environmental temperature gradients and the plurality of second segmented fluid channels are integrated into each of the walls of the second elongated monolithic member.

14. The system of claim 1 wherein the means for delivering a modulated fluid circulates the fluid heat transfer medium at a first temperature through the plurality of first segmented fluid channels and circulates the fluid heat transfer medium at a second through the plurality of second segmented fluid channels.

15. The method of claim 7 wherein the first and second side walls of the first elongated monolithic member define exterior portions that are exposed to fluctuating environmental conditions and the plurality of first segmented individual fluid channels are integrated into the first and second side walls and wherein the second and third side walls of the second elongated monolithic member define exterior portions that are exposed to fluctuating environmental conditions and the plurality of second segmented individual fluid channels are integrated into the third and fourth side walls.

16. The method of claim 7 wherein the first and second side walls of the first elongated monolithic member define exterior portions that are exposed to fluctuating environmental conditions and the plurality of first segmented individual fluid channels are integrated into each of the walls of the first elongated monolithic member and wherein the second and third side walls of the second elongated monolithic member define exterior portions that are exposed to fluctuating environmental conditions and the plurality of second segmented individual fluid channels are integrated into each of the walls of the second elongated monolithic member.

17. The method of claim 7 wherein step (c) comprises distributing the fluid heat transfer medium at a first temperature through the plurality of first segmented individual fluid channels and distributing the fluid heat transfer medium at a second temperature through the plurality of second segmented individual fluid channels.

* * * * *